United States Patent [19]

Li et al.

[11] Patent Number: 5,077,213

[45] Date of Patent: Dec. 31, 1991

[54] RECOMBINANT VACCINIA VIRUS

[75] Inventors: Zai-Ping Li; Yuan Wang, both of Shanghai, China

[73] Assignee: Shanghai Institute of Biochemistry, Chinese Academy of Sciences, Shanghai, China

[21] Appl. No.: 269,593

[22] Filed: Nov. 10, 1988

[51] Int. Cl.$^5$ .............................................. C12N 7/01
[52] U.S. Cl. .................................................. 435/235.1
[58] Field of Search ................... 435/69.1, 69.3, 172.3, 435/235, 320, 240.2, 240.21, 235.1; 935/12, 32, 48, 50, 57

[56] References Cited

U.S. PATENT DOCUMENTS 4,442,205 4/1984 Hamer et al. ...................... 435/69.1
4,769,330 9/1988 Paoletti et al. ..................... 435/172.3

OTHER PUBLICATIONS

Cheng et al., *J. of Virology*, 11/86, vol. 60, pp. 337–344, Hepatitis B Virus Large Surface Protein is not Secreted but is Immunogenic.
Cheng et al., *J. of Virology*, 4/87, vol. 61, pp. 1286–1290, Selective Synthesis and Secretion of Particles Composed of HBV Middle S Protein.
Paoletti et al., *PNAS*, 1/84, vol. 81, pp. 193–197, Construction of Live Vaccines Using Genetically Engineered Pox Viruses.
Jawetz et al., *Review of Medical Microbiology*, 1974, Chpt. 36, p. 419.

*Primary Examiner*—Richard A. Schwartz
*Attorney, Agent, or Firm*—Nixon & Vanderhye

[57] ABSTRACT

A recombinant vaccinia virus, effective in combatting hepatitis B infections in humans, is provided. The virus has incorporated therein the entire HBsAg gene, and is capable of expressing in and secreting from animal (including human) cells, in particulate form, all three of the constituent protein epitopes S, preS2 and preS1 constituting the proteinaceous surface antigen of hepatitis B virus. The recombinant vaccinia virus is prepared by recombination of a selected vaccinia virus strain of very low toxicity towards mammals with an expression plasmid containing the HBsAg sequence and the promoter sequence thereof in operative registry therewith, this sequence being provided at a location interposed within a gene sequence common to the expression plasmid and the vaccinia viral genome. This recombinant virus can be used as a novel live vaccine of low toxicity and also as a system for the production of secretable HBsAg particles with all of the three components, which can be applied as a novel sub-unit vaccine.

5 Claims, 5 Drawing Sheets

FIG. 1
CONSTRUCTION OF pGJP-5

B : BamHI
C : ClaI
E : EcoRI
H : HindIII
Pv: PvuII
R : RsaI
S : SalI
Sm: SmaI
X : XhoI
Xb: XbaI

FIG. 3

FIG. 4  PRODUCTION OF HBsAg BY HUMAN TK⁻143 CELLS INFECTED WITH vTLS-1 x——x IN CULTURE MEDIUM
•——• INSIDE CELLS

RECOMBINANT VACCINIA VIRUS

FIELD OF THE INVENTION

This invention relates to virology, and more specifically to vaccines for combatting hepatitis B virus in humans.

BACKGROUND OF THE INVENTION

Viral hepatitis B is a widely-spread, extremely harmful disease. It has been reported that approximately 200,000,000 people are chronically infected with hepatitis B virus (HBV), and numerous deaths result from it and from conditions associated with it.

In the sera of some HBV infected patients, there are 42 nm infectious virus particles comprising viral surface antigen (HBsAg) which is the proteinaceous coating of the viral particle, viral core antigen (HBcAg) and viral DNA. In addition to the whole virus particle, the blood of infected individuals contains smaller (20 to 22 nm) spherical and tubular forms that are made up of HBsAg. The HBsAg particles can induce specific antibodies and bestow immunity against infection. However, isolation of the particles from the blood is too expensive, and supplies are too limited, to permit their successful use in mass vaccination in areas where HBV is highly endemic. Besides, there might occur potential hazards due to undiscovered pathogens. Accordingly, alternative methods of producing HBV surface antigens are actively being sought.

HBsAg consists of three envelope proteins of different sizes. They are encoded in the same reading frame by the HBsAg gene, but starting from three different translation initiator ATG codons. The three proteins are the S protein (or major protein with 226 amino acids, encoded by the S region of the HBsAg gene; the minor middle surface protein (MS protein) which contains an extra 55 amino acids attached to the N-terminus of S-protein, i.e. having a total of 281 amino acids, the extra 55 amino acids being encoded by the preS2 region of the gene and containing the receptor for polymerized human serum albumin (pHSA); and minor large surface (LS) protein encoded by all three preS1, preS2 and S regions of the gene, and consisting of about 400 amino acids. MS protein and LS protein are found mainly on the envelope of the viral particle, and in HBsAg particles of sera from infectious patients.

Since HBsAg particles can induce specific antibodies and bestow immunity against infection, their biology and application to vaccine preparation have attracted wide attention. For the most part research was focused on the S-protein, but more recently on the MS and LS proteins as well. Since the MS and LS contain additional epitopes not present on the S protein, their inclusion in synthetic or recombinant vaccines has been suggested (Milich, D. R., G. B. Thornton, A. R. Neurath, S. B. Kent, M. L. Michel, P. Tiollais and F. V. Chisari (1985) Science 228. 1195-1199).

BRIEF DESCRIPTION OF THE PRIOR ART

Vaccinia virus has been used in the past to express antigens from a variety of different viruses, including HBV. By DNA recombination techniques, the required genes for expression of the appropriate proteins are inserted into vaccinia virus, and the recombinant vaccinia virus introduced into appropriate cells for expression of the proteins. The recombinant virus itself may be used as a live vaccine. Alternatively, the recombinant virus may be replicated in cells to express and preferably secrete the antigens which can then be used as the basis of a vaccine.

Cheng et al, J. Virol, (1986) Vol 60, No. 2, p 337-344, describe the construction of a recombinant vaccinia virus that contained the predicted coding segment for the large surface protein (LS), i.e. the entire HBsAg gene, under the control of a vaccinia virus promoter. They infected CV-1 cells with the recombinant vaccinia virus. The infected cells apparently did not secrete the LS protein, although it was synthesized in the cells. Furthermore, Moss and Flexner wrote in *Annual Reviews Immunology* (1987) Vol. 5, p. 305-324, that the large form of HBsAg "is not secreted as a particle and even interferes with secretion of the major HBsAg when cells are infected simultaneously with two recombinants".

Paoletti, E. et al, *Proc. Natl. Acad. Sci. USA*. (1984) Vol 81, p 193-197 describe the construction of potential live vaccines using recombinant vaccinia viruses, for both hepatitis B and herpes simplex. The hepatitis B surface antigen HBsAg is reported to be synthesized in vitro and secreted from infected cells. No identification of the three individual envelope proteins of HBsAg, or secretion thereof, is reported by Paoletti et al.

SUMMARY OF THE INVENTION

It is an object of the present invention to provide a novel recombinant vaccine effective against hepatitis B infections in humans.

It is a further object of the invention to provide a process for preparing such a hepatitis B vaccine.

The present invention provides a recombinant vaccinia virus containing the complete HBsAg gene, said virus being capable of expressing in and secreting from animal cells (which term includes human cells) HBsAg, in particulate form, and all three of the constituent protein epitopes S, preS2 and preS1 constituting the proteinaceous envelope of the hepatitis B virus. Accordingly, it provides the basis for a faster-acting anti-hepatitis vaccine for administration to humans, since the secretion of all of the proteins from the cells into the body fluids after administration can be expected to lead to the most rapid induction of the complete range of antibodies required in the human body for full protection against hepatitis B viral infections. The recombinant vaccinia virus according to the present invention also allows for enhanced production of S protein, MS protein and LS protein useful in the preparation of anti-hepatitis B compositions. Immunogenicity of HBsAg is far stronger in a preparation containing S, MS and LS compared to S alone.

The present invention also provides a process of preparing a recombinant vaccinia virus capable of expressing in and secreting from animal cells all three of the constituent proteins S, MS and LS constituting HBsAg, which comprises selecting a strain of vaccinia virus of very low toxicity towards mammals, constructing by recombinant DNA techniques an expression plasmid containing the HBsAg sequence and a promoter sequence thereof in appropriate registry therewith, infecting viable cells with the selected vaccinia virus strain and transfecting with the constructed expression plasmid so as to cause recombination thereof and to prepare recombinant vaccinia virus containing said HBsAg sequence and promoter sequence, selecting the recombinant vaccinia virus firstly on the basis of a selectable 
marker introduced thereto by said plasmid, and secondly for a capacity to cause the secretion from cells all three HBsAg epitopes of S, preS2 and preS1.

BRIEF REFERENCE TO THE DRAWINGS

DESCRIPTION OF THE PREFERRED EMBODIMENTS

Strains of vaccinia virus of very low toxicity towards mammals include those described and characterized in reference 9 listed below. Specific examples of such preferred strains are the Tiantan strain and the Guang 9 strain. These strains are known and reported, and available in the People's Republic of China, from National Institute for the Control of Pharmaceutical and Biological Products, Ministry of Health of China. Use of such vaccinia strains has the added advantage, that recombinant vaccinia produced therefrom will have very low toxicity when used as a live vaccine.

A suitable expression plasmid contains, in addition to the HBsAg and promoter sequence, an antibiotic resistance gene such as ampicillin resistance ($Ap^r$) to allow for selection of plasmid in E coli thereof by growth in an antibiotic-containing medium, and an additional marker for incorporation into the vaccinia virus on recombination, to form the basis for selection of the cells containing recombinant virus from others. Appropriately, this additional marker is an inoperative thymidine kinase gene ($TK^-$) which is sufficiently similar to the TK gene in natural vaccinia virus to permit insertion in replacement of the natural TK gene on recombination. Thus, the expression plasmid preferably carries the HBsAg and promoter sequence at a location interrupting the TK gene, so that the sequences constituting the TK gene are present in large part to permit recombination with natural vaccinia virus, but the TK gene is rendered inoperative by this interruption. The recombinants can then be selected out on the basis of TK negativity in host cells.

Referring now to FIG. 1, a plasmid pGJ-1 is constructed from the known plasmid vector pWR13 and the DNA of Guang 9 strain vaccinia virus, by digestion with restriction enzyme Hind III. Plasmid pWR13 has an ampicillin resistance marker gene $Ap^r$ and a polylinker sequence with a Hind III site. The resultant plasmid pGJ-1 has the TK gene derived from the vaccinia virus and the $Ap^r$ from the plasmid. It is next restricted and ligated appropriately to remove excess sequences and produce plasmid pGJ-2 also having TK sequence and $Ap^r$ marker. Next it is modified to introduce a SalI linker sequence, forming plasmid pGJ-7.

Another batch of known plasmid pWR-13 is restricted and ligated with plasmid pVC-1 using SalI as restriction enzyme. Plasmid pVC-1 has a $P_{7.5}$ promoter which it is required to put into operative association eventually with the HBsAg sequence to allow expression of the latter. The $P_{7.5}$ promoter sequence is merely exemplary of a number of promoters which can be used for this purpose. The $P_{7.5}$ sequence is conveniently bounded by restriction sites so that it can be excised therefrom and inserted into the polylinker sequence of pWR13, to produce plasmid pWR/VC1-22 after appropriate ligation.

Using the Sal I and EcoR I sites of pGJ-7 and pWR/VC1-22, followed by ligation, these two plasmids are combined into plasmid pGJP-5 in which the $P_{7.5}$ sequence from pWR/VC1-22 is inserted into the TK sequence from pGJ-7, this interruption rendering the TK sequence inoperative.

As shown in FIG. 2, plasmid pGJP-5 is used to construct plasmid pLS-1 according to the invention. The other starting material for this is known plasmid pADR-1 which contains the entire HBsAg expression sequence indicated on the drawing by its protein sequences preS1.preS2.S. It also has various restriction sites and an ampicillin resistance gene as shown. First, it is treated to introduce a Bam H1 restriction site (B) upstream of the HBsAg sequence, thereby producing plasmid pADR-2B. This can then be restricted and ligated with pGJP-5 to produce pLS-1, which as illustrated has the promoter sequence $P_{7.5}$ derived from pGJP-5 disposed upstream of and in operative association with the HBsAg sequence, both within the TK sequence. This plasmid pLS-1 is therefore $TK^-$, but capable of expressing HBsAg in a cell. It therefore has $TK^-$ available as selectable marker for in vivo recombination with vaccinia virus. The interruption in the TK sequence is however sufficiently minor that pLS-1 still shows marked affinity for the TK gene in unmodified vaccinia virus.

The novel vaccinia virus of the present invention may be prepared using normal vaccinia virus and plasmid pLS-1 by recombination in the live cells. As noted, this invention uses vaccinia virus strains of low toxicity, e.g. Guang 9 strain or Tiantan strain. It is particularly preferred to use primary cells such as chick embryo cells as the host cell. The use of such primary cells, as opposed to established cell lines, enables the production of purer live vaccines as well as the sub-unit vaccine, since it avoids the risk of contamination with impurities present in established cell lines.

Thus as illustrated diagrammatically in FIG. 3, plasmid pLS-1 and Guang 9 or Tiantan strain vaccinia virus 12 are introduced into a chick embryo cell generally designated 14. The interrupted TK sequence 16 on pLS-1 and the natural intact TK sequence 18 on the virus 12 exhibit natural affinity for one another, will come into contact with one another and in a few cases will be exchanged between the plasmid and the virus, by the process of recombination. Accordingly there is produced, in minor quantities, a recombinant vaccinia virus 20, characterized by the presence of an interrupted and therefore inoperative TK sequence. It has the complete HBsAg sequence and operative promoter therefor. Cells containing the recombinant virus 20 can therefore be selected on the basis of the $TK^-$ characteristic, and replicated in order to produce greater quantities of the virus for use as a live vaccine. The M, S and LS proteins of HBsAg are all expressed and secreted from the cells to provide a hepatitis vaccine of high potency.

The invention is further described for illustrative purposes in the following specific examples.

MATERIALS AND METHODS

1. Klenow fragment of DNA polymerase I was obtained from Boehringer, BstEII enzyme from Biolabs, low melting agarose and BamHI linker from B.R.L., and the other restriction enzymes and T4DNA ligase from the Reagent Enzyme Group of the Shanghai Institute of Biochemistry, Academia Sinica.

2. Human TK$^-$143 cells, deficient in the TK (thymidine kinase) gene were supplied by Dr. B. Moss, The Laboratory of Viral Diseases, National Institute of Allergy and Infectious Diseases, Bethesda, Maryland 20892, and grown in DMEM (Dulbecco Modified Eagle Medium) containing 25 $\mu$g/ml of 5-bromodeoxyuridine (BUdR) and 5% fetal calf serum. The Tiantan strain of vaccinia virus was propagated on primary chick embryonic cells (CEC). These cells were prepared from ten days old embryos and grown in DMEM medium containing 10% calf serum.

3. Transfection of cells: CEC cells were infected with Vaccinia Tiantan virus. Two hours later they were transfected with calcium phosphate precipitated DNA containing 10 $\mu$g plasmid DNA and 15 $\mu$g fish sperm DNA. Fresh medium was added to the cells after cultivation at 37° C. for 4–6 hours, and the cells were harvested after 48 hours.

4. Isolation and purification of DNA: vaccinia viral DNA was isolated directly from infected cells by the method of Esposito et al as described in reference 1 listed herein. Plasmid DNA was purified on Sepharose 2B column after alkaline treatment, by the procedure described in reference 2 listed herein.

5. Construction of plasmid DNA: the plasmid pGJP-5 constructed from the Guang-9 strain of vaccinia virus was described by Wu et al in *Acta Biochimica et Biophysica Sinica* (1987) Vol. 19, No. 5, p. 397–405. The pADR-1 plasmid containing HBsAg gene of Hepatitis B virus was described by Wu et al, *Scientia Sinica(B)* (1983), Vol. 26, No. 9, p954–960. To construct the new plasmids pADR-2 and pLS-1, in each instance the vector plasmid and DNA fragment were joined by T4DNA ligase after digestion with appropriate restriction enzyme, and transformed into either E. coli HB101 in the case of plasmid pADR-2B, or E. coli JM83 in the case of plasmid pLS-1.

6. Selection of recombinant virus: TK$^-$ recombinant virus was selected by a selective plaque assay in the presence of BUdR according to Weir et al (see reference 3 listed herein). The TK$^-$ virus obtained were subjected to further screening to select for clones that produced a high level secretion from host cells of all three of the S, preS2 and preS1 epitopes of HBsAg.

7. Determination of HBsAg: HBsAg content was determined by the AUSRIA kit from Abbott Co., using HBsAg reference from Paul-Ehrlich Institute of West Germany.

8. Analysis of polypeptide composition: SDS-polyacrylamide gel electrophoresis was performed according to Laemmli (see reference 4 listed herein) using silver staining for detection, and Western blot was performed as described in reference 5 listed herein.

9. To determine preS1 and preS2 by enzyme-linked immunosorbent assay (ELISA), protein sample was adsorbed to microtitre plates coated with anti-preS1 (MA18/7) or anti-preS2 (Q19/10) monoclonal antibodies from Dr. W. H. Gerlich of West Germany, and treated subsequently with peroxidase-linked anti-S, as described in reference 6 listed herein. The determination of polymerized human serum albumin (pHSA) receptor activity was carried out as described in reference 7 listed herein.

EXAMPLE 1

Preparation and Construction of the Expression Plasmid pLS-1

Figure 1:
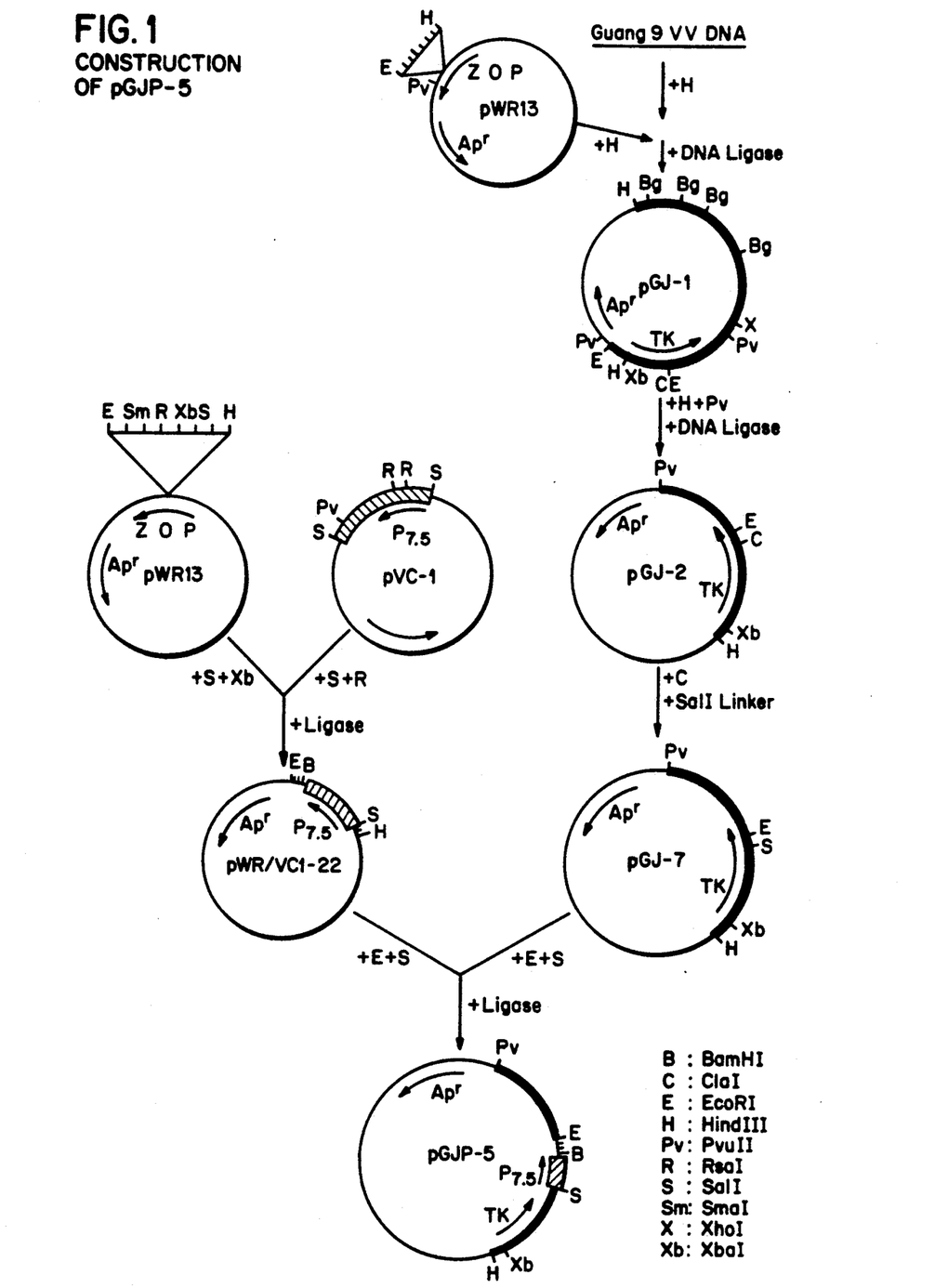
FIG. 1 is a diagrammatic illustration of the preparation of general expression vector plasmid pGJP-5.
Figure 2:
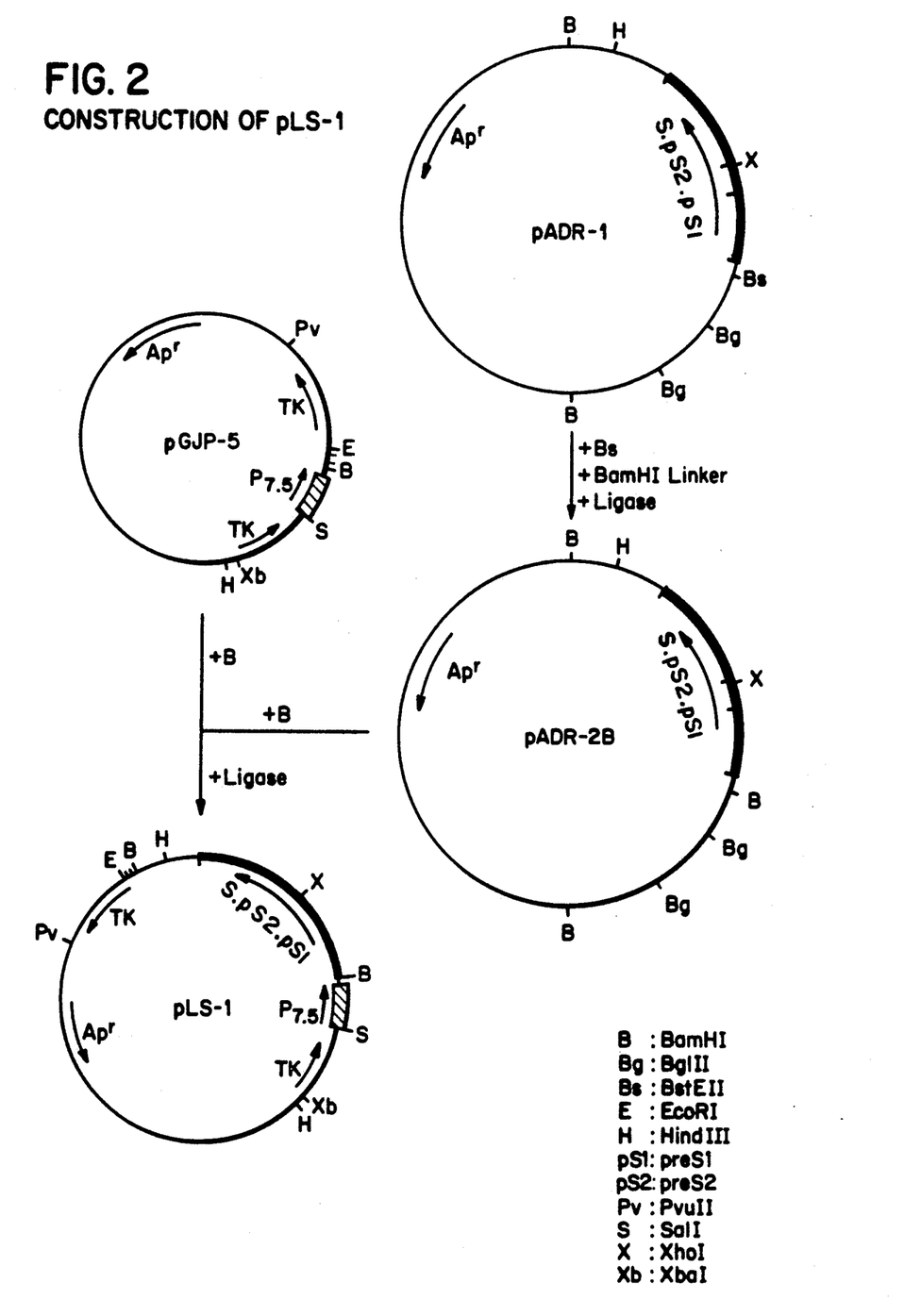
FIG. 2 is a similar diagrammatic illustration of the preparation of novel plasmid vector pLS-1 of the invention, using pGJP-5 as one of the starting materials.
Figure 3:
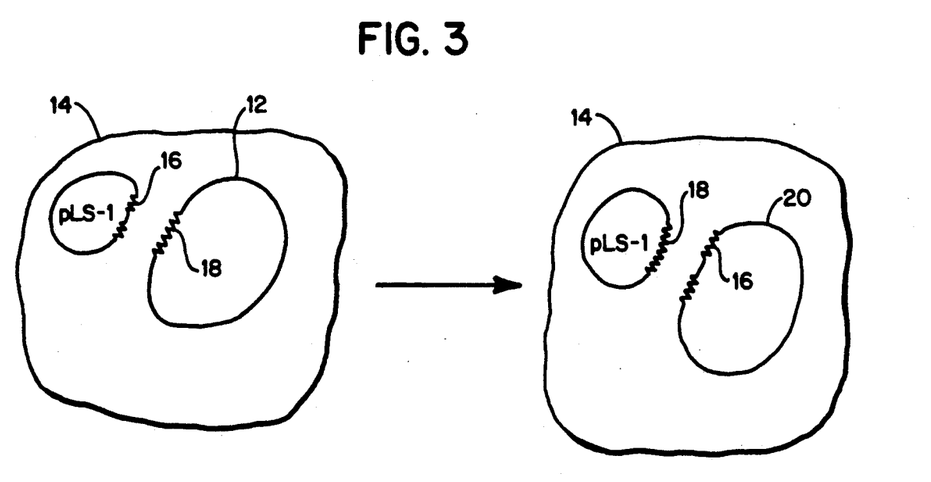
FIG. 3 is a diagrammatic illustration of the recombination of a vaccinia virus with pLS-1 to prepare the novel recombinant vaccinia virus according to the invention.

The procedure followed was generally as illustrated in FIG. 1, for the preliminary steps to prepare pGJP-5, and FIG. 2, for the final steps of preparation of pLS-1.

(a) Preparation of pGJP-5 (FIG. 1)

This preparation followed the experimental procedures described in reference 8 listed herein:

The low toxicity vaccinia Guang-9 strain virus was restricted by HindIII. The HindIII-J fragment was cloned into the pWR13 plasmid to yield pGJ-1, which has an EcoRI site on the pWR13 portion, and another EcoRI site in the TK gene within HindIII-J from Guang-9. Removal of the pWR13 EcoRI site and part of the Guang-9 DNA outside of TK gene yielded pGJ-2. Conversion of a ClaI site next to the remaining EcoRI site to a SalI site gave pGJ-7. Insertion of the promoter of the P$_{7.5}$ protein (7.5K vaccinia protein) into the TK gene on pGJ-7, between the EcoRI and SalI sites led to pGJP-5.

(b) Preparation of pLS-1 (FIG. 2)

The vector plasmid pGJP-5 contains the vaccinia TK gene, the promoter P$_{7.5}$ (promoter for the vaccinia 7.5k protein), and a polylinker. The vaccinia TK gene sequence provided a homologous sequence and selection marker for the in vivo recombination between plasmid and vaccinia virus DNA. HBsAg gene was derived from the cloned adr sub-type genome in pADR-1. The BstEII restriction site in front of the preS region was altered to a BamHI site to result in the pADR-2B plasmid. This plasmid thus possesses a BamHI site both upstream and downstream to the HBsAg LS-protein gene. Restriction with BamHI yielded an intact HBsAg LS-protein gene of 1.8 kb, which was inserted into the BamHI site in the polylinker of the vector plasmid pGJP-5, and selected by means of in situ hybridization to give the HBsAg LS-protein gene-containing expression plasmid pLS-1.

EXAMPLE 2

Analysis of Expression Plasmid pLS-1

The plasmid pGJP-5 was 4.5 kb in size. Insertion of the 1.8 kb HBsAg gene fragment led to 6.3 kb for the recombinant plasmid pLS-1. There were unique BamHI, EcoRI and HindIII sites on plasmid pGJP-5. Thus restriction of pGJP-5 with any of these enzymes gave a single band of 4.5 kb. In the HBsAg gene-containing insert, there were unique HindIII and XhoI sites, but no EcoRI site. Accordingly restriction of pLS-1 by EcoRI still gave a single band of 6.3 kb, to which the vector contributed 4.5 kb, and the HBsAg insert contributed 1.8 kb.

The HindIII site in pGJP-5 is located upstream to P$_{7.5}$ at a distance of 0.9 kb from the BamHI site. The HindIII site in the HBsAg gene fragment is downstream to the S region, 1.5 kb away from the BamHI site upstream to the preS region, and 0.3 kb away from the downstream BamHI site. The small fragment obtained from pLS-1 by HindIII restriction was 2.4 kb, and not 1.2 kb, demonstrating that the HBsAg gene insert and the $P_{7.5}$ gene are codirectional.

The XhoI site is located in the preS2 region near the S region, and there is no XhoI site in vector plasmid pGJP-5. Consequently, after digestion of pLS-1 by BamHI and XhoI, the 1.8 kb BamHI fragment disappeared, forming the 0.5 kb and 1.3 kb fragments. The 0.5 kb fragment contains the preS region, and the 1.3 fragment contains the S region.

EXAMPLE 3

Construction and Analysis of Recombinant Vaccinia Virus vTLS-1

Recombinant vaccinia virus vTLS-1 was constructed through in vivo recombination. Two hours after infection of CEC cells with vaccinia Tiantan virus, the cells were transfected with calcium phosphate precipitated pLS-1. 48 hours later, the cells were harvested and selected for recombinant vaccinia virus. In the pLS-1, $P_{7.5}$ and HBsAg genes were inserted into the vaccinia viral TK gene, thereby destroying the activity of the TK gene. Thus the recombinant vaccinia virus was $TK^-$. By employing the $TK^-143$ human cells, such $TK^-$ recombinant virus were selected through plaque selection in the presence of BUdR. Further purification and selection among the $TK^-$ recombinant virus clones for the capacity to produce a high level secretion from infected host cells of all three of the S, preS2 and presS1 protein epitopes of HBsAg Yielded the recombinant vaccinia virus vTLS-1.

We have also analyzed the construction of vTLS-1 by means of DNA hybridization using $^{32}P$-labelled DNA fragments containing S and preS as probes.

EXAMPLE 4

Measurement of vTLS-1 HBsAg Expression

We measured the expression of HBsAg by vTLS-1 in human $TK^-143$ cells by radioimmunoassay (RIA). 48 hours after infecting $3 \times 10^6$ $TK^-143$ cells by 0.1 PFU (plaque forming unit) virus per cell, the total quantity of HBsAg expressed was 2.1 μg, with 1.8 μg in the culture medium, and 0.3 μg in the cells.

Figure 4:
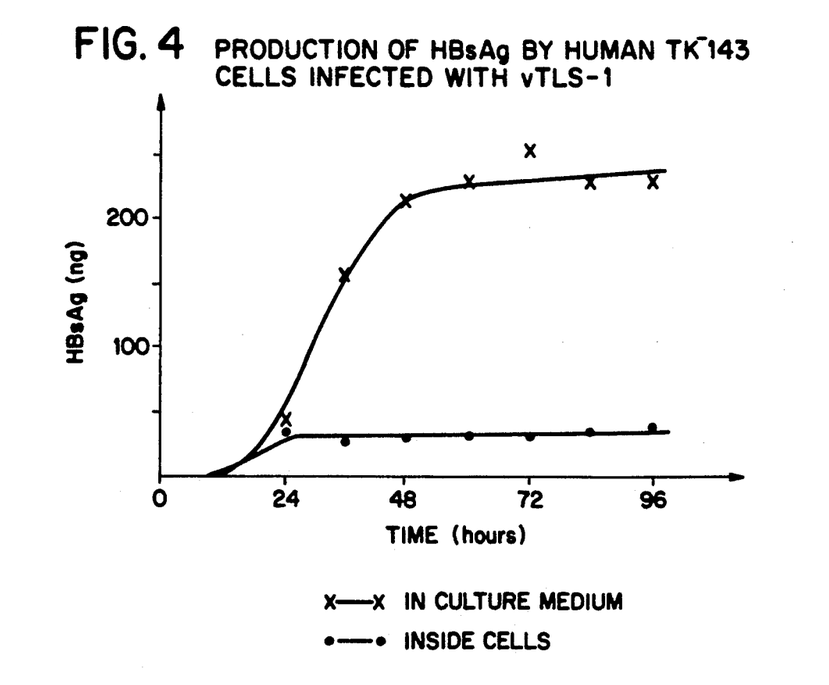
FIG. 4 is a time-course graph of HBsAg production derived from Example 4 below.

Using the same method we measured the time dependence of expression of vTLS-1 in $TK^-143$ cells. $1 \times 10^5$ human $TK^-143$ cells were infected by $1 \times 10^4$ PFU units of the virus. After 2 hours, the supernate was removed, and 2 ml of DMEM containing 10% fetal calf serum was added. Culture medium and cells were sampled at 12 hour intervals and analyzed for HBsAg. The time course obtained showed that HBsAg content increased for 48 hours post-infection, thereafter approaching a saturation level (FIG. 4).

EXAMPLE 5

Properties of vTLS-1 Expression Products

Since there are three different translational initiation sites with the same reading frame in the HBsAg gene in vTLS-1, there could be more than one component in the expressed products included in the HBsAg measurement.

Figure 5A:
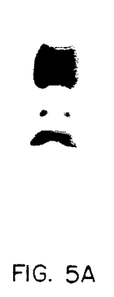
FIG. 5 shows affinity chromatography results from Example 5 below.
Figure 5B:
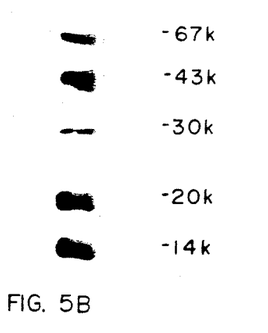

Further to assess the protein composition of HBsAg expressed by vTLS-1 in human $TK^-143$ cells, electrophoretic analysis of the protein products was performed. The cells were infected with 0.1 PFU virus per cell. After 48 hours, the supernate was collected, and virus was removed by centrifugation at 16,000 rpm for one hour. The HBsAg in the supernate was purified by affinity chromatography on monoclonal anti-S IgG linked Sepharose 4B, electrophoresed on SDS-polyacrylamide gel, and silver stained. The results showed three protein bands around 24K, 27K and 30–42-K—FIG. 5. Of these, 24K represents the S protein, 27K the glycosylated S protein, and 30–42K the larger proteins. The larger proteins were polydispersed, as might be expected from different extents of glycosylation.

Figure 6A:
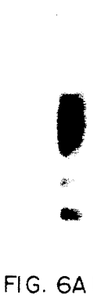
FIG. 6 shows Western blot characterization results from Example 5 below.
Figure 6B:
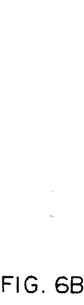
Figure 6C:
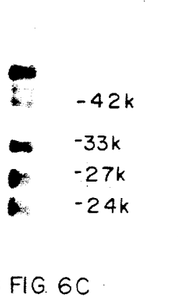

The identities of these HBsAg components were further tested by Western blot. Following SDS-polyacrylamide gel electrophoresis, the protein bands were transferred to nitrocellulose membrane, reacted with anti-S, hybridized with $^{125}I$-Protein A, and autoradiographed (FIG. 6). The results of the Western blot were in basic agreement with those of electrophoresis confirming the three protein bands as HBsAg components. The products of vTLS-1 reacted very well with anti-preS1 (MA18/7) and anti-preS2 (Q19/10) monoclonal antibodies again proving the presence of the larger proteins among the vTLS-1 expression products, and their secretion from human $TK^-143$ cells. At the same time, the vTLS-1 expression products exhibited pHSA-receptor (for polymerized human serum albumin) activity. This activity is provided by the preS2 region in the product proteins. These results are presented in Table 1 below.

TABLE 1

The properties of HBsAg purified from culture medium of vTSL-1 infected Human $TK^-143$ cells investigated by ELISA pr pHSA receptor assay. In each case, an OD value (at 490 nm) less than 0.4 indicates a negative result.

| Virus | preS1[a] | preS2[b] | pHSA receptor |
|---|---|---|---|
| vTLS-1 | 1.96 | 1.60 | >2.05 |
| vTH-2[c] | 0.30 | 0.31 | 0.20 |

[a]Using preS1 specific monoclonal antibody MA18/7
[b]Using preS2 specific monoclonal antibody Q19/10
[c]The vTH-2 recombinant virus, derived from vaccinia Tiantan, contains only the S region of the HBsAg gene, and is therefore incapable of synthesizing either the preS2 or preS1 epitope.

The experimental results demonstrate that we have succeeded in constructing a recombinant vaccinia virus vTLS-1 containing an intact HBsAg gene, which is capable of producing, as well as resulting in the secretion of, all three of the HBsAg S, preS2 and preS1 protein epitopes after infection of human $TK^-143$ cells. By immunoassay with monoclonal anti-preS1, the presence of preS1 protein epitope secreted into the culture medium was revealed. The preS2 component of the HBsAg products retained its pHSA-receptor activity, as well as reactivity toward anti-preS2.

Figure 7:
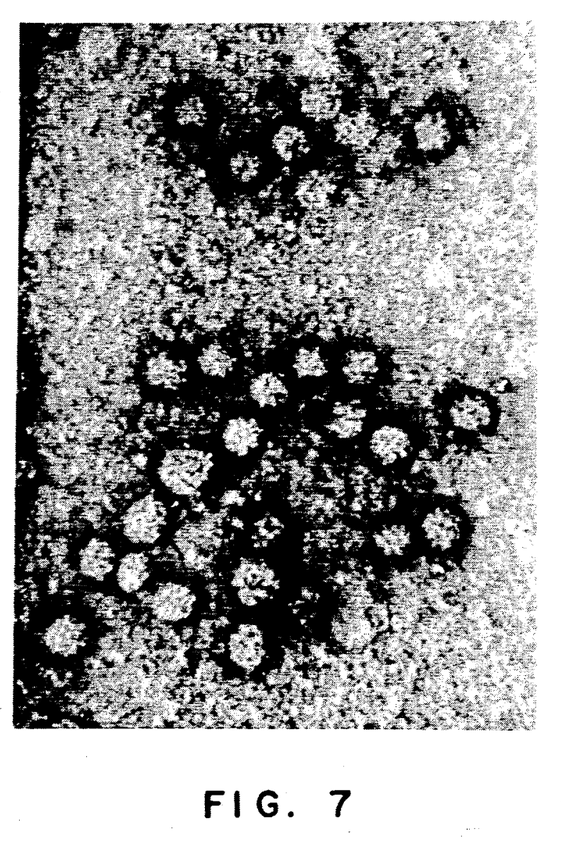
FIG. 7 is an electron micrograph of HBsAg particles produced in Example 5 below.

In our experiments infecting human $TK^-143$ cells, the expression products included S, preS2 and preS1 protein epitopes and formed particles of uniform size of about 22 nm. The secretable particles collected from the culture medium could be observed by electron microscopy (FIG. 7) and their nature has been further confirmed as follows:

1. CsCl gradient centrifugation with particle distribution determined by pHSA binding assay: The density of the particles was 1.26 g/ml, similar to that of the major S particle.
2. RIA of HBsAg which gives positive results only for HBsAg in particulate state.

3. ELISA with monoclonal antibodies against preS1 and preS2.

The particle formation of HBsAg is critical for a sub-unit vaccine, since the immunogenicity is 3 orders higher than that of free antigen molecules. So, the secretable particles of HBsAg containing MS and LS offer a novel sub-unit vaccine which is high in immunogenicity by virtue of its inducing antibodies against all the epitopes of HBsAg.

Previously Cheng et al, "Hepatitis B Virus Large Surface Protein Is Not Secreted but Is Immunogenic When Selectively Expressed by Recombinant Vaccinia Virus" J. Virol. (Nov. 1986) Vol. 60, p. 337-344, have constructed a recombinant vaccinia virus v73 containing the HBsAg gene, similar to the vTLS-1 virus described herein. As they pointed out, up to the time of their study, "Synthesis of S has been obtained in eucaryotic cells by recombinant DNA methods. In some cases both MS and S were made, but in no case has LS been demonstrated." The v73 virus for the first time led to the intracellular synthesis of the LS protein, but with no secretion and no particle formation. The vTLS-1 virus described herein thus represents the first instance in which a recombinant vaccinia virus containing HBsAg has led to the synthesis as well as secretion of LS protein-containing particles as defined by the presence of both the preS2 and preS1 epitopes.

The preS region of the HBsAg LS protein is endowed with a number of important biological properties. It can induce neutralizing antibodies. Milich, D. R. et al, in "Enhanced Immunogenicity of the Pre-S Region of Hepatitis B Surface Antigen", Science (1985) 228, 1195-1199 have shown that the preS region is more antigenic than the S region of HBsAg, eliciting a faster immune response than the S region. In addition, LS protein is relatively enriched among the HBsAg in the serum of patients of acute hepatitis. The PreS region of LS protein also participates in viral attack on liver cells, and exerts a modulating action on virus assembly. Therefore its investigation not only serves the preparation of HBV vaccine, but also provides new directions for diagnosis and treatment. The successful construction and expression of the recombinant vaccinia vTLS-1 virus enables us to obtain large quantities of HBsAg LS protein containing an intact preS region, and makes possible further advances in research on the biology of this protein. It provides a novel live vaccine, as well as a novel sub-unit vaccine against hepatitis B infections.

EXAMPLE 6

Toxicity Determination of Vaccinia Virus Strains

The toxicities of various vaccinia viral strains including WR strain used in the prior art by Cheng et al. and the Tiantan-derived Guang 9 strain used herein were assessed for $LD_{50}$ in mice with the results illustrated in Table 2. The $LD_{50}$ for Tiantan is similar to that of Guang-9. The very low toxicities of the Tiantan and Guang-9 strains apply to humans as well. There have been tens of millions of inoculations with these two strains of vaccinia for the prevention of smallpox.

TABLE 2

| LETHALITY OF VACCINIA VIRUS STRAINS IN MICE | |
| --- | --- |
| Viral Strain | $LD_{50}$ (in plaque number) |
| WR | <17 |
| Guang-9 | 5692 |

We claim:

1. A recombinant vaccinia virus effective in combating hepatitis B infections in humans, said virus having been prepared by recombination in a viable chick embryo cell of a vaccinia viral strain selected from the group consisting of Guang 9 and Tiantan strains with expression plasmid pLS-1, followed by selection of the viable vaccinia virus and recovery of the recombinant virus therefrom, said virus having incorporated therein the entire HBsAg gene, and being capable of expressing in and secreting from animal cells, in particulate form, all three of the constituent protein epitopes S, preS2 and preS1 constituting the proteinaceous surface antigen of the hepatitis B virus.

2. The combinant vaccinia virus of claim 1, wherein selection takes place on the basis of TK characteristic of the recombinants introduced via plasmid pLS-1.

3. A process of preparing a recombinant vaccinia virus capable of expressing in and secreting from host cells all three of the protein epitopes S, preS2 and preS1 constituting HBsAg, which comprises selecting a strain of vaccinia virus from the group consisting of Guang 9 and Tiantan strains, infecting viable chick embryo cells with the said selected vaccinia virus strain and transfecting said virus strain therein with expression plasmid pLS-1 so as to cause recombination thereof and to prepare recombinant vaccinia virus containing HBsAg sequence and promoter sequence derived from pLS-1, selecting recombinant vaccinia virus on the basis of a selectable marker introduced thereto by said plasmid pLS-1, and recovering the recombinant vaccinia virus so selected.

4. The process of claim 3 wherein the TK characteristic derived from pLS-1 is used as the selectable marker for selecting recombinant vaccinia virus.

5. The process of claim 4 wherein the recombinant vaccinia virus is further selected on the basis of capacity to secrete all three S, preS2 and preS1 epitopes.

* * * * *